(12) United States Patent
Coleman et al.

(10) Patent No.: US 6,479,630 B1
(45) Date of Patent: Nov. 12, 2002

(54) HUMAN PURINERGIC $P_{2U}$ RECEPTOR

(75) Inventors: Roger Coleman, Mountain View, CA (US); Janice Au-Young, Berkeley, CA (US); Susan G. Stuart, Montara, CA (US); Karl J. Guegler, Menlo Park, CA (US)

(73) Assignee: Incyte Genomics, Palo Alto, CA (US)

( * ) Notice: Subject to any disclaimer, the term of this patent is extended or adjusted under 35 U.S.C. 154(b) by 0 days.

(21) Appl. No.: 09/102,710

(22) Filed: Jun. 22, 1998

Related U.S. Application Data

(62) Division of application No. 08/459,046, filed on Jun. 2, 1995, now Pat. No. 6,008,039.

(51) Int. Cl.$^7$ ............................................. G07K 14/705
(52) U.S. Cl. ........................ 530/350; 530/326; 930/10
(58) Field of Search ................................ 530/350, 300, 530/324, 326; 930/10; 424/185.1

(56) References Cited

FOREIGN PATENT DOCUMENTS

WO     WO 96/05302     2/1996

OTHER PUBLICATIONS

"Peptide Hormones" (Ed. J. A. Parsons) University Rudinger, In Park Press, Baltimore, pp. 1–7, 1976.*
Alonso–Torre et al., "Calcium Responses Elicited by Nucleotides in Macrophages," *J. Biol. Chem.* 268 (25) :18640–18647 (Sep, 5, 1993).
Parr et al., "Cloning and expression of a human $P_{2U}$ nucleotide receptor, a target for crystic fibrosis pharmacotherapy," *Proc. Natl. Acad. Sci. USA* 91:3275–3279 (Apr. 1994).
Watson et al., *The G–Protein Linked Receptor Facts Book*, Academic Press, San Diego, CA, pp. 20–31 (1994).
Bolander, Franklyn F., *Molecular Endocrinology*, 2nd ed., Academic Press, San Diego, CA, pp. 162–176 (1994).
Rice et al., "Cloning and Expression of the Alveolar Type II Cell $P_{2U}$—Purinergic Receptor," *Am. J. Respir. Cell Mol. Biol.* 12:27–32 (1995).
Benirschke et al., *Pathology of the Human Placenta*, 2nd ed., Springer—Verlag, New York, New York, pp. 542–635 (1992).
Fisher et al., "Human cytotrophoblast invasion," *Semin. Cell Biol.* 4(3):183–188 (Abstract only) (Jun. 1993).
Graham et al., "Mechanisms of placental invasion of the uterus and their control," *Biochem. Cell Biol.* 70:867–874 (1992).
Smith et al., "Nutrient Transport Pathways Across the Epithelium of the Placenta," *Ann. Rev. Nutr.* 12:183–206 (1992).
Schneider, H., "Placental transport function," *Reprod. Fertil. Dev.* 3 (4) :345–353 (Abstract only) (1991).
Hay, W.W., Jr., "The placenta. Not just a conduit for maternal fuels," *Diabetes* 40S (2) :44–50 (Abstract only) (Dec. 1991).
Makiya et al., "Placental Alkaline Phosphatase as the Placental IgG Receptor," *Clin. Chem.* 38 (12) :2543–2545 (1992).
Herrera–Gonzalez et al., "Fetal–Maternal Immune Interaction: Blocking Antibody and Survival of the Fetus," *Dev. Comp. Immunol.* 17–1–18 (1993).
Holmgren et al., "The expression of PDGF alpha– and beta–receptors in subpopulations of PDGF–producing cells implicates autocrine stimulatory loops in the control of proliferation in cytotrophoblasts that have invaded the maternal endometrium," 6(3) :219–231 (Abstract only) (1992).
Mitchell et al., "Cytokine Networking in the Placenta," *Placenta* 14:249–275 (1993).
Rutanen, E.M., "Cytokines in reproduction," *Ann. Med.* 25 (4) : 343–347 (Abstract only) Aug. 1993).
Erb et al., "Functional expression and photoaffinity labeling of a cloned $P_{2U}$ purinergic receptor" *Proc. Natl. Acad. Sci. USA* 90:10449–10453 (Nov. 1993).
Mullis et al., "Specific enzymatic amplification of DNA in vitro: the polymerase chain reaction," *Cold Spring Harbor Symp. Quant. Biol.* 51:263–273, Part 1 (Abstract only) (1986).
Sarkar et al., "Restriction–site PCR: A Direct Method of Unknown Sequence Retrieval Adjacent to a Known Locus by Using Universal Primers," *PCR Methods and Applications* (1993).
Triglia et al., "A procedure for in vitro amplification of DNA segments that lie outside the boundaries of known sequences," *Nucleic Acids Res.* 16(16):8186 (1988).
Lagerstrom et al., "Capture PCR: efficient amplification of DNA fragments adjacent to a known sequence in human and YAC DNA," *PCR Methods Applic.* 1 (2) :111–119 (Abstract only) (Nov. 1991).
Parker et al., "Targeted gene walking polymerase chain reaction," *Nucleic Acids Res.* 19 (11) :3055–3060 (1991).
Zilberberg et al., *Analytical Biochemistry*, 209:203–205 (Feb. 1993).
Barnes, "PCR amplification of up to 35–kb DNA with high fidelity and high yield from Y bacteriophage templates", *Proc. Natl. Acad. Sci. USA*, 19:2216–2220 (Mar. 1994).
Communi et al., (Direct Submission), GenBank Sequence Database (Accession X97058), National Center for Biotechnology Information, National Library of Medicine, Bethesda, Maryland 20894 (Apr. 1996).

* cited by examiner

Primary Examiner—Gary L. Kunz
Assistant Examiner—Robert C Hayes
(74) *Attorney, Agent, or Firm*—Incyte Genomics, Inc.

(57) ABSTRACT

The present invention provides nucleotide and amino acid sequences that identify and encode a novel purinergic $P_{U2}$ receptor (PNR) expressed in human placenta. The present invention also provides for antisense molecules to the nucleotide sequences which encode PNR, expression vectors for the production of purified PNR, antibodies capable of binding specifically to PNR, hybridization probes or oligonucleotides for the detection of PNR-encoding nucleotide sequences, genetically engineered host cells for the expression of PNR, and diagnostic tests based on PNR-encoding nucleic acid molecules or antibodies produced against the polypeptide PNR.

3 Claims, 7 Drawing Sheets

```
                    9                  18                 27              36                 45                 54
5' ATG GAA TGG GAC AAT GGC ACA GAC CAG GCT CTG GGC TTG CCA CCC ACC TGT
   Met Glu Trp Asp Asn Gly Thr Asp Gln Ala Leu Gly Leu Pro Pro Thr Cys 63                  72                 81              90                 99                108
   GTC TAC CGC GAG AAC TTC AAG CAA CTG CTC CCA CCT GTG TAT TCG GCG GTG
   Val Tyr Arg Glu Asn Phe Lys Gln Leu Leu Pro Pro Val Tyr Ser Ala Val 117                 126                135             144                153                162
   CTG GCG CCT GCC CTC CCG CTG AAC ATC TGT GTC ATT ACC CAG ATC TGC TCC
   Leu Ala Pro Ala Leu Pro Leu Asn Ile Cys Val Ile Thr Gln Ile Cys Ser 171                 180                189             198                207                216
   CGC CGG GCC CTG ACC CGC ACG GCC GTG TAC ACC CTA AAC CTT GCT CTG GAC
   Arg Arg Ala Leu Thr Arg Thr Ala Val Tyr Thr Leu Asn Leu Ala Leu Asp 225                 234                243             252                261                270
   CTG CTA TAT GCC TGC TCC CTG CCC CTG CTC ATC TAC AAC TAT GCC CAA GGT GAT
   Leu Leu Tyr Ala Cys Ser Leu Pro Leu Leu Ile Tyr Asn Tyr Ala Gln Gly Asp
```

Figure 1A

```
        279             288             297             306             315             324
CAC TGG CCC TTT GGC GAC TTC GCC TGC CGC CTG GTC CGC TTC CTC TTC TAT GCC
His Trp Pro Phe Gly Asp Phe Ala Cys Arg Leu Val Arg Phe Leu Phe Tyr Ala 333             342             351             360             369             378
AAC CTG CAC GGG AGG ATC CTC TTC ACC TGC ATC AGC TTC CAG CGC TAC CTG
Asn Leu His Gly Arg Ile Leu Phe Thr Cys Ile Ser Phe Gln Arg Tyr Leu 387             396             405             414             423             432
GGC ATC TGC CAC CCG CTG GCC CCC TGG CAC AAA CGT GGG GGC CGG GCT GCC
Gly Ile Cys His Pro Leu Ala Pro Trp His Lys Arg Gly Gly Arg Ala Ala 441             450             459             468             477             486
TGG CTA GTG TGT GTA GCC GTG TGG CTG GCC GTG ACA ACC CAG TGC CTG CCC ACA
Trp Leu Val Cys Val Ala Val Trp Leu Ala Val Thr Thr Gln Cys Leu Pro Thr 495             504             513             522             531             540
GCC ATC TTC GCT GCC ACA GGC ATC CAG CGT AAC CGT ACT GTC TGT TAT GAC CTC
Ala Ile Phe Ala Ala Thr Gly Ile Gln Arg Asn Arg Thr Val Cys Tyr Asp Leu 549             558             567             576             585             594
AGC CCG GCC CCT GCC CTG ACC CAC TAT ATG CCC TAT GGG ATG GCT CTC ACT GTC
Ser Pro Ala Pro Ala Leu Thr His Tyr Met Pro Tyr Gly Met Ala Leu Thr Val 603             612             621             630             639             648
ATC GGC TTC CTG CTG CCC TTT GCT GCC CTG CTG CTG GCC TGC TAC TGT CTC CTG GCC
Ile Gly Phe Leu Leu Pro Phe Ala Ala Leu Leu Leu Ala Cys Tyr Cys Leu Leu Ala
```

Figure 1B

```
     657             666             675             684             693             702
TGC CGC TGC CGC CAG GAT GGC CCG GCA GAG CCT GTG GCC CAG GAG CGG CGT
Cys Arg Cys Arg Gln Asp Gly Pro Ala Glu Pro Val Ala Gln Glu Arg Arg 711             720             729             738             747             756
GGC AAG GCC CGC ATG GCC CGC GTG GTG GCT GTC TTT GGC ATC AGC TTC
Gly Lys Ala Arg Met Ala Arg Val Val Ala Val Phe Gly Ile Ser Phe 765             774             783             792             801             810
CTG CCT TTT CAC ATC ACC AAG ACA GCC TAC CTG GCA GTG CGC TCG ACG CCG GGC
Leu Pro Phe His Ile Thr Lys Thr Ala Tyr Leu Ala Val Arg Ser Thr Pro Gly 819             828             837             846             855             864
GTC CCC TGC ACT GTA TTG GAG GCC TTT GCA GCG GCC TAC AAA GGC ACG CGG CCG
Val Pro Cys Thr Val Leu Glu Ala Phe Ala Ala Tyr Lys Gly Thr Arg Pro 873             882             891             900             909             918
TTT GCC AGT GCC AAC AGC GTG CTG GAC CCC ATC CTC TTC TAC CAG AAG
Phe Ala Ser Ala Asn Ser Val Leu Asp Pro Ile Leu Phe Tyr Thr Gln Lys 927             936             945             954             963             972
AAG TTC CGC CGG CGA CCA CAT GAG CTC CTA CAG CTC AAA CTC ACA GAC AAA TGG CAG
Lys Phe Arg Arg Arg Pro His Glu Leu Leu Gln Lys Leu Thr Asp Lys Trp Gln

981
AGG CAG GGT CGC 3'
Arg Gln Gly Arg
```

Figure 1C

```
 1  M A A G L D S W N S T I N G T W E G D E    Rat Purinergic Receptor
 1  M E - - - - - - - - - W D N G T D - - - -  Q A   SEQ ID NO:2

21  L G Y - - - K C R F N E D F K Y V L L P    Rat Purinergic Receptor
11  L G L P P T C V Y R E N F K Q L L L P      SEQ ID NO:2

38  V S Y G V V C V L G L C L N V V A L Y I    Rat Purinergic Receptor
31  P V Y S A V L A P A L P L N I C V I T Q    SEQ ID NO:2

58  F L C R L K T W N A S T T Y M F H L A V    Rat Purinergic Receptor
51  I C T S R R A L T R T A V Y T L N L A L    SEQ ID NO:2

78  S D S L Y A A S L P L L V Y Y A Q G D      Rat Purinergic Receptor
71  P D L L Y A C S L P L L I Y N Y A Q G D    SEQ ID NO:2

98  H W P F S T V L C K L V R F L F Y T N L    Rat Purinergic Receptor
91  H W P F G D F A C R L V R F L F Y A N L    SEQ ID NO:2
```

FIGURE 2A

```
118  Y C S I L F L T C I S V H R S L G V L R    Rat Purinergic Receptor
111  H G R I L F L T C I S F Q R Y L G I C H    SEQ ID NO:2

138  P L H S L - R W G H A R Y A R R V A A V    Rat Purinergic Receptor
131  P L A P W H K R G G R R A A W L V C V A    SEQ ID NO:2

157  V W V L V L A C Q T P V L Y F V T T S V    Rat Purinergic Receptor
151  V W L A V T T Q C L P T A I F A A T G I    SEQ ID NO:2

177  R G T R I T C H D T S D R E L F S H F V    Rat Purinergic Receptor
171  Q R N R T V C Y D L S P P A L A T H Y M    SEQ ID NO:2

197  A Y S S V M L G L L F A V P F S I I L V    Rat Purinergic Receptor
191  P Y G M A L T V I G F L L P F A A L L A    SEQ ID NO:2

217  C Y V L M A R R L L K P A Y G T T G L P    Rat Purinergic Receptor
211  C Y C L L A C R L C R Q D G P A E P V A    SEQ ID NO:2
```

FIGURE 2B

```
237  R A K R - K S V R T I A L V L A V F A L   Rat Purinergic Receptor
231  Q E R R G K A A R M A V V A A V F G I     SEQ ID NO:2

256  C F L P F H V T R T L Y Y S F R S L - D   Rat Purinergic Receptor
251  S F L P F H I T K T A Y L A V R S T P G   SEQ ID NO:2

275  L S C H T L N A I N M A Y K I T R P L A   Rat Purinergic Receptor
271  V P C T V L E A F A A A Y K G T R P F A   SEQ ID NO:2

295  S A N S C L D P V L Y F L A G Q R L V R   Rat Purinergic Receptor
291  S A N S V L D P I L F Y F T Q K K F R R   SEQ ID NO:2

315  F A R D A K P A T E P T P S P Q A R R K   Rat Purinergic Receptor
311  - - - - - - - - - - - - - - - - - - - -  SEQ ID NO:2

335  L G L H R P N R T D T V R K D L S I S S   Rat Purinergic Receptor
311  - - - - R P H - - - - E L L Q K L        SEQ ID NO:2
```

FIGURE 2C

320 TD K W Q R Q G R
355 D D S R R T E S T P A G S E T K D I R L    Rat Purinergic Receptor SEQ ID NO:2

FIGURE 2D

HUMAN PURINERGIC $P_{2U}$ RECEPTOR

This application is a divisional application of U.S. application Ser. No. 08/459,046, filed Jun. 2, 1995 now U.S. Pat. No. 6,008,031.

The purinergic $P_{2U}$ or nucleotide receptor is an integral part of the plasmalemma of various mammalian cell types. The $P_{U2}$ receptor described in this application is most similar to a G-protein coupled surface receptor from rat. These receptors are associated with cells such as neutrophils, endothelial cells, and fibroblasts in the immune, neural, muscular, pulmonary and vascular systems. $P_{2U}$ receptors stimulate phosphoinositide metabolism and the release of intracellular $Ca^{++}$ in the presence of extracellular nucleotides, particularly UTP or ATP. In macrophages, $Mg^{++}$ inhibits the response of $P_{2U}$ to ATP (Alonso-Torre S R and A Trautmann (1994) J Biol Chem 268:18640–47); and in lung epithelial cells, stimulation of the $P_{2U}$ receptor by nucleotides modulates chloride secretion. $P_2$ receptors have a very low affinity for adenosine and are not activated by the methylxanthine antagonists, caffeine and theophylline.

The $P_{2U}$ receptor is in the $P_2$ receptor family for which the common structural features have been described: 1) seven hydrophobic domains, 2) consensus N-linked glycosylation sequences near the amino terminus, 3) a number of residues common to G-protein coupled receptors ($asn^{51}$, $asp^{79}$, $cys^{106}$, and $cys^{183}$), and 4) potential phosphorylation sites in the third intracellular and carboxyterminal domains (Parr C E et al (1994) Proc Natl Acad Sci 91:3275–79).

In addition to $P_{2U}$, there are four other $P_2$ receptor subtypes. The $P_{2X}$ receptor mediates smooth muscle response following sympathetic nerve stimulation and contains an intrinsic cation channel. The $P_{2Y}$ receptor is found in smooth muscle and vascular tissue where it induces vasodilation in response to nitric oxide. The $P_{2Z}$ receptor is found primarily on mast or other immune cells, and when activated by ATP, it appears to cause cell permeabilization. The $P_{2T}$ receptor, which is only found on platelets, inhibits adenylate cyclase and stimulates the release of intracellular calcium ions. In contrast, P1 receptors are stimulated by adenosine rather than nucleotides.

The G-protein coupled receptors (T7G) characteristically contain seven hydrophobic domains which span the plasma membrane and form a bundle of antiparallel α helices. These transmembrane segments are designated by roman numerals and account for many of the structural and functional features of the receptor. In most cases, the bundle of helices forms a binding pocket; however, the binding site for bulky molecules includes the extracellular N-terminal segment or one or more of the three extracellular loops. Binding may also alter the receptor's intracellular configuration (Watson S and Arkinstall S (1994) The G-Protein Linked Receptor Facts Book, Academic Press, San Diego, Calif.).

The activated receptor interacts with an intracellular G-protein complex which mediates further intracellular signalling activities, generally the production of second messengers such as cyclic AMP (cAMP), phospholipase C, inositol triphosphate, or ion channel proteins. Coupling to G-proteins involves a variable sequence in the C-terminal 10–20 amino acids of the third internal loop between the transmembrane segments V and VI and the intracellular segment immediately C-terminal to transmembrane segment VII. Interaction with Gq also requires the N-terminal 10–20 amino acids of the third internal Both structural and functional features of T7Gs allow their classification into five categories: β-type, muscarinic-type, neurokinin-type, nonneurokinin-type, and miscellaneous (Bolander F F (1994) Molecular Endocrinology, Academic Press, San Diego, Calif.); each of which are discussed below. $P_{2U}$ is a β-type receptor and has structural features shared with β-adrenergic, α-adrenergic, histamine, dopamine, and serotonin receptors. These receptors have a short N-terminus with two conserved N-glycosylation sites, a moderately short third internal loop, and a long C-terminus containing a Ser/Thr-rich region. All adrenergic receptors elevate cAMP or intracellular calcium.

The novel purinergic receptor which is the subject of this patent application was identified among the cDNAs derived from a placental library. Incyte Clone 179696 is a novel homolog of RNU09402, a G-protein coupled surface receptor from rat (Rice WR et al (1995) Am J Respir Cell Molec Biol 12:27–32). Purinergic receptors of the: placenta are likely found on immune or vascular cells and appear to play an important role in signal transduction and other specialized functions of the placenta as briefly described below.

Placenta

The placenta is a thickened discoid temporary organ that acts as the site of interchange of substances between the maternal and fetal bloodstreams. Such substances include oxygen, nutrients, hormones, excretory products, humoral antibodies (immunoglobulin G, IgG), drugs, viruses, or any other chemical or infectious agent that may be present in the maternal circulation.

The placenta consists of a fetal part derived from the chorion, one of the extraembryonic surrounding membranes of the conceptus and of a maternal part (decidua basalis) derived from the region of endometrium that underlies the implantation site. The placenta is thus the only organ composed of cells derived from two individuals. The boundary between maternal and fetal tissues is marked by extracellular products of necrosis referred to as fibrinoid. The anatomy of the human placenta is discussed in detail in Benirschke and Kaufmann, (1992) Pathology of the Human Placenta, Springer-Verlag, New York City, pp 542–635.

Development

The late blastocyst consists of an inner cell mass that gives rise to the embryo and an outer, single layer of trophoblast cells that encloses the blastocyst cavity. Following implantation, trophoblasts become highly invasive, erode and attach to the secretory endometrium. This invasive process involves matrix-degrading metalloproteinases (MMPs) and tissue inhibitors of metalloproteinases (TIMPs), adhesion receptors and their extracellular ligands, and the class I human leukocyte antigen-G (HLA-G) molecule. The invasive process is reviewed in Fisher and Damsky (1993 Semin Cell Biol 4(3):183–188) and in Graham and Lala (1992 Biochem Cell Biol 70:867–874).

Trophoblasts give rise to two layers. The inner layer is composed of individual cells, cytotrophoblasts, which have high proliferative potential. The outer layer is composed of syncytial cells, syncytiotrophoblasts, which invade the endometrium and become surrounded by cavernous spaces (lacunae) filled with maternal blood. Finger-like extensions of the cytotrophoblasts grow into these protrusions and act as primary placental villi. The capillaries found in this tissue are a part of the embryonic circulation. Tufted extensions of part of the chorion or chorionic villi are associated with the decidua basalis and develop into the large, elaborately branched outgrowths of the villous chorion. The syncytiotrophoblasts remain until the end of pregnancy, but by the fifth month of gestation, most of the cytotrophoblasts begin to fuse with the syncytiotrophoblast. The few remaining cytotrophoblasts form a discontinuous basal layer.

Chorion

The chorion or fetal part of the placenta has a chorionic plate at the point where the chorionic villi arise. The finger-like villi extend into the endometrial lacuna which are filled with maternal blood released under pressure from the endometrial spiral arteries. A connective tissue core in which the fetal blood vessels develop is derived from extraembryonic mesenchyme surrounded by syncytiotrophoblast and cytotrophoblast cell layers.

During pregnancy, surface area of the villi increases dramatically. The surfaces of the villi are active in the exchange of substances between fetal and maternal circulatory systems. Receptors within the apical microvilli facilitate transport of glucose, amino acids, and IgG from mother to fetus. The mechanism for IgG movement is similar to that of IgA across epithelia. The transport of various materials, particularly nutrients, by the placenta is reviewed in Smith et al (1992 Ann Rev Nutrition 12:183–206) and Schneider (1991 Reprod Fertil Dev 3:345–353). The placenta is more than a simple conduit for nutrients; it engages in considerable metabolic activity contributing to the quality and quantity of nutrients supplied to the fetus (cf. Hay (1991) Diabetes 40S:44–50).

Although the villi express foreign paternal as well as maternal antigens and a maternal immune response would be expected against the fetal "allograft", the fetus is not usually rejected. The type of Fetal factors such as major histocompatibility complex (MHC) I (but not MHC II) and low antigen density and maternal response (suppressor cells and molecules) all contribute to a complex and unique tolerance. The absence of MHC II may be particularly significant, since MHC II has been implicated in the rejection of organ allografts.

Decidua Basalis

The function of the endometrium is to support the implantation and development of the embryo. During each menstrual cycle, the most superficial layer or functionalis, undergoes dramatic changes in preparation for these events. During proliferative phase in the first half of the cycle, rising estrogen levels stimulate the division of epithelial and stromal cells in the functionalis. The uterine lining is ready by the time of ovulation at day 14.

During the secretory phase in the second half of the cycle, endometrial cells differentiate in response to rising levels of progesterone. Beginning as early as day 15, glycogen appears in the basal region of the epithelial cells and displaces the nuclei. By day 18, the glycogen is dispersed, the nuclei have returned to a basal portion of the cell, Golgi are prominent apically, and secretion is maximal. Concurrently, the nuclear envelope indents to form a channel system associated with the nucleolus. This system is believed to facilitate a rapid transfer of ribosomal components between the nucleus and the cytoplasm. Uterine secretions contain significant amounts of glucose and specific glycoproteins such as PP14 which may confer immunosuppression in preparation for contact with the "foreign" embryo.

Implantation induces a decidual response that is characterized by pronounced changes in the endometrial stroma. Fibroblast-like cells transform into large, active decidual cells that become an important component of the decidua basalis. Predecidual cells, which appear in the endometrial stroma during the fourth week of every menstrual cycle, form a cuff around small vessels in the stroma. The vessels become more permeable as menstruation or placental development approaches.

The predecidual cells appear to limit embryo invasion, play a role in embryo nutrition, and protect fetal tissue from rejection. These cells produce prolactin (and possibly relaxin), secrete prostaglandins, and have receptors for both estrogen and progesterone. The effects of estrogen and progesterone on the endometrium, both during the cycle and following implantation, are complemented and implemented by a variety of growth factors. Insulin-like growth factors (IGFs) have a major role in the stimulation of endometrial cell division. With rising levels of progesterone after ovulation, IGF-binding proteins, including the placental protein PP12 synthesized by the predecidual cells, are secreted. IGF-binding proteins reduce the availability of IGFs and thus play a role in the shift from a proliferative to a secretory endometrium.

The decidua basalis supplies arterial blood to and receives venous blood from the lacunae situated between the villi. Although the maternal blood vessels are open during implantation, the fetal vessels remain intact. Fetal and maternal blood do not mix, except on rare occasions at the end of pregnancy. During this period when the cytotrophoblast is no longer continuous and the capillaries of the villi are very close to the surface, a very slight exchange of blood may occur. At that time, the walls of the fetal capillaries are separated from the maternal blood only by the syncytiotrophoblast.

During pregnancy, cells from the connective tissue stroma of the decidua basalis and a lesser number of cells from the decidua parietalis and decidua capsularis form decidual cells. These large, slightly basophilic cells have many profiles of rough endoplasmic reticulum, long mitochondria, and membrane-limited granules contained in club-shaped projections of the cell surface. Decidual cells are more numerous during the first half of pregnancy, contain a nucleus with a prominent nucleolus, and secrete prolactin which is similar to pituitary prolactin.

At the end of a full-term pregnancy, the placenta has the shape of a thick disk. The umbilical cord usually arises from the center of the placenta and connects the circulation of the fetus with the fetal placental circulation. Fetal venous blood reaches the placenta through the two umbilical arteries which branch and ultimately give rise to the vessels of the chorionic villi. In these villi, the fetal blood receives oxygen, loses its $CO_2$ and returns to the fetus through the umbilical vein. Although the chorionic villi are submerged in maternal blood, the fetal placental blood is isolated by the structures that form the placental barrier—the endothelium and basal lamina of the fetal capillaries; the mesenchyme in the villus interior; the basal lamina of the trophoblast; the cytotrophoblast, during the first half of pregnancy; and the syncytiotrophoblast.

The placenta is permeable to several substances and normally transfers oxygen, water, electrolytes, carbohydrates, lipids, proteins, vitamins, hormones, antibodies, and some drugs from the maternal to the fetal circulation. Carbon dioxide, water, hormones, and residual products of metabolism are transferred from fetal blood to maternal blood. The complexity of this bidirectional transport reflects the function of the placental layers as the equivalent of three organ systems—respiratory, gastrointestinal, and urinary. The mechanism of transport is extremely varied, ranging from simple diffusion of gases to many types of receptor-mediated transport including the active transport of amino acids and a special shuttle mechanism for IgG. IgG is the only immunoglobulin which crosses the placental barrier, enters fetal circulation, and protects the newborn against infection. Makiya and Stignrand (1992 Clin Chem 38:2543–45) suggest that placental alkaline phosphatase binds the Fc portion of IgG and acts as the placental IgG receptor.

Maternal Immunologic Tolerance of Fetal Tissue

Villi expressing foreign (paternal) antigens are exposed directly to maternal blood. Even though a maternal immune response occurs, fetal tissue is not typically rejected. Low expression of MHC I, absence of MHC II, and suppression of maternal response contribute to this unique tolerance. The trophoblast which is the true allograft and comes in contact with maternal blood, does not express classical MHC antigens. Occasionally, maternal IgG may harm the fetus relative to Rhesus factor (Rh) or maternal immune thrombocytopenic purpura.

An understanding of how the trophoblast/fetus escapes rejection might allow development of rational strategies for combating pregnancy disorders, such as preeclampsia or intrauterine growth retardation, having an immunological basis. The fetal-maternal immune interaction is reviewed in Herrera-Gonzalez and Dresser (1993 Dev Comp Immunol 17:1–18).

Placental Hormones

Soon after implantation, fetal villi begin to control maternal physiology creating an optimal environment for fetal development. Immediately after implantation, the syncytiotrophoblast synthesizes human chorionic gonadotropin (HCG), a glycoprotein hormone that mimics the effects of luteinizing hormone (LH) through the first few months of gestation. HCG has a subunit identical to that of LH and follicle-stimulating hormone (FSH). LH acts on and maintains the corpus luteum by stimulating estrogen and progesterone synthesis.

Beginning at about eight weeks into gestation, the syncytiotrophoblast assumes the role of the corpus luteum and begins to secrete estrogen and progesterone. The steroid hormones progesterone and estrogen are made by both kinds of trophoblast, but estrogen production requires the metabolic cooperation of the fetal adrenal cortex and liver. The syncytiotrophoblast which continues to produce these hormones throughout gestation utilizes both maternal and fetal androgen precursors to form estrogens and massive amounts are released into the maternal bloodstream.

Placental progesterone is synthesized from cholesterol obtained primarily from circulating low-density lipoprotein (LDL). Membranes of the microvilli provide surface area for LDL receptors. LDL is initially shuttled into lysosomes and cholesterol is released by the action of acid hydrolases. Then the cholesterol is transported to mitochondria where it is acted upon by enzyme complexes within the tubular cristae.

The syncytiotrophoblast is also the chief source of human chorionic somatomammotropin (HCS), a glycoprotein hormone with both lactogenic and growth-promoting activity. HCS is similar to growth hormone and has effects on maternal carbohydrate, fat, and protein metabolism. As maternal utilization of fatty acids increases, available glucose is reserved for the fetus. HCS has its major effect, in conjunction with prolactin, on development of the mammary gland.

Cytotrophoblasts produce significant amounts of platelet-derived growth factor-beta (PDGF-$\beta$) as well as the PDGF-$\alpha$ and -$\beta$ receptors (Holmgren et al (1992) Growth Factors 6:219–231). PDGF may play a role in cytotrophoblast proliferation. The action of various cytokines on the placenta is reviewed in Mitchell et al (1993 Placenta 14:249–275) and Rutanen (1993 Ann Med 25:343–347).

Pathology of the Placenta

Preeclampsia, now referred to as "pregnancy-induced hypertension" (PIH), deserves special note. Common in pregnancy, preeclampsia is characterized by sudden development of hypertension, edema, and proteinuria. More severe toxemia or eclampsia includes convulsions and coma which may jeopardize both mother and fetus. The pathological changes of the placenta found in PIH are decidual arteriolopathy, infarcts, abruptio placenta, and Tenney-Parker changes.

The principal cause of preeclampsia is still unknown although it is certain that the disease relates to the presence of placental tissue, since the delivery of the placenta (or hydatidiform mole) ends the disease process. An obliterative thickening of arterial walls and a reduced number of small arteries in the villi have been observed and may explain the increase in vascular resistance in PIH. Another cause of uneven blood flow may be vasoconstriction. While the blood levels of the vasoconstrictor, angiotensin II, are not increased, uterine vascular responsiveness is greatly increased. Vasoconstriction may be induced by a reduction of unopposed thromboxane and angiotensin II. Reduced oxygen tension in the maternal blood supplied to the intervillous lacunae may also play a role.

Many types of infections by viruses, bacteria, mycoplasmas, or parasites cause pathological changes in the placenta. Infections may ascend from the endocervical canal, or they may reach the placenta through the maternal blood. Rarely are they acquired by amniocentesis, chorionic villus sampling, amnioscopy, percutaneous umbilical blood sampling, or intrauterine fetal transfusions. Some infections cause gross and microscopic changes of the placenta, while others leave few characteristic or specifically recognizable traces.

Other disorders of the placenta include, but are not limited to, abruptio placentae;

placenta previa; placental or maternal floor infarction; placenta accreta, increta, and percreta; extrachorial placentas; chorangioma; chorangiosis; chronic villitis; placental villous edema; widespread fibrosis of the terminal villi; intervillous thrombi; hemorrhagic endovasculitis; erythroblastosis fetalis; and nonimmune fetal hydrops. The pathology of the human placenta and decidua is discussed in Benirschke and Kaufmann, (1992) Pathology of the Human Placenta, Springer-Verlag, New York City pp. 542–635, and in Naeye (1992), Disorders of the Placenta, Fetus, and Neonate: Diagnosis and Clinical Significance, Mosby Year Book, St. Louis Mo.

SUMMARY OF THE INVENTION

The subject invention provides a unique nucleotide sequence which encodes a novel human purinergic $P_{2U}$ receptor (PNR). Incyte Clone No 179696 was used to identify and clone the full length cDNA (pnr) from the placenta cDNA library.

The invention also comprises the use of this PNR or its variants to intercede in physiologic or pathologic conditions and include diagnosis or therapy of activated or inflamed cells and/or tissues with pnr nucleic acids, fragments or oligomers thereof. Aspects of the invention include the antisense DNA of pnr; cloning or expression vectors containing pnr; host cells or organisms transformed with expression vectors containing pnr; a method for the production and recovery of purified PNR from host cells; purified protein, PNR, which can be used to generate antibodies for diagnosis or therapy of activated or inflamed cells and/or tissues.

DESCRIPTION OF THE FIGURES

FIG. 1 A–C shows the nucleotide (SEQ ID NO:1) and amino acid (SEQ ID NO:2) alignments of the consensus sequence for PNR. The primers XLR (278–298) and XLF (587–610) for full length cloning are shown as arrows.

FIG. 2A–D displays the amino acid alignment of PNR (SEQ ID NO:2) with rat purinergic receptor (RNU09402; SEQ ID NO:3). The residues by which the $P_{2U}$ receptor is defined (e.g., $asn^{44}$, $asp^{72}$, $cys^{99}$, and $cys^{177}$ of SEQ ID NO:2) are shown (Parr et al, supra).

DETAILED DESCRIPTION OF THE INVENTION

Definitions

As used herein, PNR, refers to purinergic receptor homologs, naturally occurring PNRs and active fragments thereof, which are encoded by mRNAs transcribed from the cDNA (pnr) of Seq ID No 1.

"Active" refers to those forms of PNR which retain the biologic and/or immunologic activities of any naturally occurring PNR.

"Naturally occurring PNR" refers to PNRs produced by human cells that have not been genetically engineered and specifically contemplates various PNRs arising from post-translational modifications of the polypeptide including but not limited to acetylation, carboxylation, glycosylation, phosphorylation, lipidation and acylation.

"Derivative" refers to PNRs chemically modified by such techniques as ubiquitination, labeling (e.g., with radionuclides, various enzymes, etc.), pegylation (derivatization with polyethylene glycol), and insertion or substitution by chemical synthesis of amino acids such as ornithine, which do not normally occur in human proteins.

"Recombinant variant" refers to any polypeptide differing from naturally occurring PNRs by amino acid insertions, deletions, and substitutions, created using recombinant DNA techniques. Guidance in determining which amino acid residues may be replaced, added or deleted without abolishing activities of interest, such as normal signal transduction, may be found by comparing the sequence of the particular PNR with that of homologous peptides and minimizing the number of amino acid sequence changes made in highly conserved regions.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, ie, conservative replacements. "Insertions" or "deletions" are typically in the range of about 1 to 5 amino acids. The variation allowed may be experimentally determined by producing the peptide synthetically or by systematically making insertions, deletions, or substitutions of nucleotides in a pnr molecule using recombinant DNA techniques and assaying the expressed, recombinant variants for activity.

Where desired, a "signal or leader sequence" can direct the polypeptide through the membrane of a cell. Such a sequence may be naturally present on the polypeptides of the present invention or provided from heterologous sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any PNR peptide must have sufficient length to display biologic and/or immunologic activity.

An "oligonucleotide" or polynucleotide "fragment", "portion", "probe" or "segment" is a stretch of nucleotide residues which is long enough to use in polymerase chain reaction (PCR) or various hybridization procedures. Oligonucleotides are prepared based on the cDNA sequence which encodes PNR provided by the present invention and are used to amplify, or simply reveal, related RNA or DNA molecules. Oligonucleotides comprise portions of the DNA sequence having at least about 10 nucleotides and as many as about 35 nucleotides, preferably about 25 nucleotides. Nucleic acid probes comprise portions of pnr sequence having fewer nucleotides than about 6 kb, preferably fewer than about 1 kb. After appropriate testing to eliminate false positives, both oligonucleotides and nucleic acid probes may be used to determine whether mRNAs encoding PNR are present in a cell or tissue or to isolate similar natural nucleic acid sequences from chromosomal DNA as described by Walsh P S et al (1992, PCR Methods Appl 1:241–50).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, Cold Spring Harbor N.Y.; or Ausubel F M et al (1989) Current Protocols in Molecular Biology, John Wiley & Sons, New York City, both incorporated herein by reference.

Recombinant variants encoding T7Gs may be synthesized or selected by making use of the "redundancy" in the genetic code. Various codon substitutions, such as the silent changes which produce specific restriction sites, may be introduced to optimize cloning into a plasmid or viral vector or to increase expression in a particular prokaryotic or eukaryotic system. Codon usage-specific mutations may also be introduced or chimeras containing the domains of related peptides added to test or modify the properties of any part of the polypeptide, particularly to change ligand-binding affinities, interchain affinities, or degradation/turnover rate.

DETAILED DESCRIPTION OF THE INVENTION

The present invention provides a unique nucleotide sequence identifying a novel homolog of the human purinergic receptor which was first identified in a human placenta cDNA library. The sequence for pnr is shown in SEQ ID No 1 and is homologous to the GenBank sequence, RNU09402 (Rice et al, supra). Because $P_{2U}$ is specifically expressed in cells active in immunity, the nucleic acid (pnr), polypeptide (PNR) and antibodies to PNR are useful in investigations of and interventions in the normal and abnormal physiologic and pathologic processes which comprise the placenta's role in immunity. Therefore, an assay for upregulated expression of PNR can accelerate diagnosis and proper treatment of conditions caused by abnormal signal transduction due to systemic and local infections, traumatic and other tissue damage, hereditary or environmental diseases associated with hypertension, carcinomas, cystic fibrosis, and other physiologic or pathologic problems.

The nucleotide sequence encoding PNR (or its complement) has numerous other applications in techniques known to those skilled in the art of molecular biology. These techniques include use as hybridization probes for Southerns or northerns, use as oligomers for PCR, use for chromosomal and gene mapping, use in the recombinant production of PNR, use in generation of anti-sense DNA or RNA, their chemical analogs and the like, and use in production of chimeric molecules for selecting agonists, inhibitors or antagonists for design of domain-specific therapeutic molecules. Uses of the nucleotides encoding PNR disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of PNR-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring PNR, and all such variations are to be considered as being specifically disclosed.

Although nucleotide sequences which encode PNR and its variants are preferably capable of hybridizing to the nucleotide sequence of the naturally occurring PNR gene under stringent conditions, it may be advantageous to produce nucleotide sequences encoding PNR or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding PNR and its derivatives without altering the encoded amino acid sequence include the production of RNA transcripts having more desirable properties, such as a greater half-life, than transcripts produced from the naturally occurring sequence.

The nucleotide sequence encoding PNR may be joined to a variety of other nucleotide sequences by means of well established recombinant DNA techniques (cf Sambrook J et al, supra). Useful nucleotide sequences for joining to pnr include an assortment of cloning vectors—plasmids, cosmids, lambda phage derivatives, phagemids, and the like—that are well known in the art and may be chosen for such characteristics as the size insert they can accommodate, their international utility, their fidelity, etc. Other vectors of interest include expression vectors, replication vectors, probe generation vectors, sequencing vectors, YAC and BAC mapping vectors, and the like. In general, these vectors may contain an origin of replication functional in at least one organism, convenient restriction endonuclease sensitive sites, and selectable markers for the host cell.

Another aspect of the subject invention is to provide for pnr-specific nucleic acid hybridization probes capable of hybridizing with naturally occurring nucleotide sequences encoding PNR. Such probes may also be used for the detection of PNR-encoding sequences and should preferably contain at least 50% of the nucleotides from any particular domain of interest from this pnr encoding sequence. The hybridization probes of the subject invention may be derived from the nucleotide sequence of the SEQ ID NO 1 or from genomic sequence including promoter, enhancer elements and introns of the respective naturally occurring pnr. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR, as described in U.S. Pat. Nos. 4,683,195; 4,800,195; and 4,965,188, provides additional uses for oligonucleotides based upon the nucleotide sequences which encode PNR. Such probes used in PCR may be of recombinant origin, may be chemically synthesized, or may be a mixture of both and comprise a discrete nucleotide sequence for diagnostic use or a degenerate pool of possible sequences for identification of closely related $P_{U2}$ or related T7G sequences.

Full length genes may be cloned from known sequence using a new method which employs XL-PCR (Perkin-Elmer, Foster City, Calif.) to amplify long pieces of DNA. This method was developed to allow a single researcher to process multiple genes (up to 20 or more) at a time and to obtain an extended (possibly full-length) sequence within 6–10 days. It replaces current methods which use labelled probes to screen libraries and allow one researcher to process only about 3–5 genes in 14–40 days.

In the first step, which can be performed in about two days, primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones. If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg Md.). The cDNA library may have been prepared with oligo dT or random primers. The advantage of using random primed libraries is that they will have more sequences which contain 5' ends of genes. A randomly primed library may be particularly useful if an oligo dT library does not yield a complete gene. Obviously, the larger the protein, the less likely it is that the complete gene will be found in a single plasmid.

Other means for producing hybridization probes for closely related sequences include the cloning of nucleic acid sequences encoding PNR or its derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate labeled nucleotides.

It is now possible to produce a DNA sequence, or portions thereof, encoding PNR and/or its derivatives entirely by synthetic chemistry. Such molecules can be inserted into any of the many available vectors using reagents and methods that are known in the art at the time of the filing of this application. Moreover, synthetic chemistry may be used to introduce mutations into the pnr sequences or any portion thereof.

The nucleotide sequence can be used to develop an assay to detect activation, inflammation, or disease associated with abnormal levels of PNR expression. The nucleotide sequence can be labeled by methods known in the art and added to a fluid or tissue sample from a patient. After an incubation period sufficient to effect hybridization, the sample is washed with a compatible fluid which contains a visible marker, a dye or other appropriate molecule(s), if the nucleotide has been labeled with an enzyme. After the compatible fluid is rinsed off, the dye is quantitated and compared with a standard. If the amount of dye is significantly elevated (or lowered, as the case may be), the nucleotide sequence has hybridized with the sample, and the assay indicates an abnormal condition such as inflammation or disease.

The nucleotide sequence for pnr can be used to construct hybridization probes for mapping that T7G gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of pnr on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

The nucleotide sequence encoding PNR may be used to produce purified PNR using well known methods of recombinant DNA technology. Among the many publications that teach methods for the expression of genes after they have been isolated is Goeddel (1990) Gene Expression Technology, Methods and Enzymology, Vol 185, Academic Press, San Diego, Calif. PNR may be expressed in a variety of host cells, either prokaryotic or eukaryotic. Host cells may be from the same species in which pnr nucleotide sequences are endogenous or from a different species. Advantages of producing PNR by recombinant DNA technology include obtaining adequate amounts of the protein for purification and the availability of simplified purification procedures.

Cells transformed with DNA encoding PNR may be cultured under conditions suitable for the expression of PNR and recovery of the protein from the cell culture. PNR produced by a recombinant cell may be secreted or may be contained intracellularly depending on the particular genetic construction used. In general, it is more convenient to prepare recombinant proteins in secreted form. Purification steps vary with the production process and the particular protein produced.

Various methods for the isolation of PNR polypeptide may be accomplished by procedures well known in the art. For example, such a polypeptide may be purified by immunoaffinity chromatography by employing the antibodies provided by the present invention. Various other methods of protein purification well known in the art include those described in Deutscher M (1990) Methods in Enzymology, Vol 182, Academic Press, San Diego, Calif.; and in Scopes R (1982) Protein Purification: Principles and Practice, Springer-Verlag, New York City, both incorporated herein by reference.

In addition to recombinant production, fragments of PNR may be produced by direct peptide synthesis using solid-phase techniques (cf Stewart et al (1969) Solid-Phase Peptide Synthesis, W H Freeman Co, San Francisco Calif.; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (ABI, Foster City, Calif.) in accordance with the instructions provided by the manufacturer. Various fragments of PNR may be chemically synthesized separately and combined using chemical methods to produce the full length molecule.

PNR for antibody induction does not require biological activity; however, the protein must be immunogenic. Peptides used to induce specific antibodies may have an amino acid sequence consisting of at least five amino acids, preferably at least 10 amino acids. They should mimic a structural portion of the amino acid sequence of the protein and may contain the entire amino acid sequence of a single domain of PNR. Short stretches of PNR amino acids may be fused with those of another protein such as keyhole limpet hemocyanin, and antibody produced against the fusion protein.

Antibodies specific for PNR may be produced by inoculation of an appropriate animal with the polypeptide or an antigenic fragment. An antibody is specific for PNR if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–37, or Huse W D et al (1989) Science 256:1275–81) or the in vitro stimulation of lymphocyte populations. Current technology (Winter G and Milstein C (1991) Nature 349:293–99) provides for a number of highly specific binding reagents based on the principles of antibody formation. These techniques may be adapted to produce molecules specifically binding particular domains of PNR.

An additional embodiment of the subject invention is the use of PNR specific antibodies or the like as bioactive agents to treat abnormal signal transduction associated with systemic and local infections, traumatic and other tissue damage, hereditary or environmental diseases associated with hypertension, carcinomas, cystic fibrosis, and other physiologic or pathologic problems.

Bioactive compositions comprising agonists, antagonists, or inhibitors of PNR may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

The examples below are provided to describe the subject invention. These examples are provided by way of illustration and are not included for the purpose of limiting the invention.

EXAMPLES

I Isolation of mRNA and Construction of the cDNA Library

Placental tissue was obtained from a term pregnancy (40 weeks gestation) of a male neonate delivered by Caesarean section. The tissue was flash frozen, ground in a mortar and pestle, and lyzed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to a paramagnetic particle (Promega Corp, Madison, Wis.) and sent to Stratagene (La Jolla, Calif.).

Stratagene prepared the cDNA library using oligo d(T) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was. excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego, Calif.) and pSHlox-1 (Novagen, Madison Wis.).

II Isolation of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified and used to reinfect fresh host cells (SOLR, Stratagene) where double-stranded phagemid DNA was produced. Because the phagemid carries the gene for β-lactamase, the newly transformed bacteria were selected on medium containing ampicillin.

A alternative phagemid purification procedure uses the QIAWELL-8 Plasmid Purification System from the QIAGEN® DNA Purification System (QIAGEN Inc, Chatsworth, Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

III Sequencing of cDNA Clones

The cDNA inserts from random isolates of the placenta library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double- stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Catalyst 800 and the Applied Biosystems 377 or 373 DNA sequencers.

IV Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification, Full Length Cloning, Sequencing and Translation

Analysis of INHERIT™ results from randomly picked and sequenced portions of clones from placenta library identified Incyte 179696 as a homolog of the purinergic receptor RNU09402. The cDNA insert comprising Incyte 179696 was fully sequenced and used as the basis for cloning the full length cDNA.

The cDNA of Incyte 179696 was extended to full length using a modified XL-PCR (Perkin Elmer) procedure. Primers were designed based on known sequence; one primer was synthesized to initiate extension in the antisense direction (XLR) and the other to extend sequence in the sense direction (XLS or XLF). The primers allowed the sequence to be extended "outward" generating amplicons containing new, unknown nucleotide sequence for the genes of interest. The primers were designed using Oligo 4.0 (National Biosciences Inc, Plymouth, Minn.). In general, primers should be 22–30 nucleotides in length, have a GC content of 50% or more, and anneal to the target sequence at temperatures about 68°–72° C. Any stretch of nucleotides which would result in hairpin structures and primer-primer dimerizations were avoided.

The placenta cDNA library was used as a template, and XLR and XLS primers were used to amplify sequences containing the gene of interest. The enzymes of the XL-PCR kit were found to provide high fidelity in the amplification providing kit instructions were followed. In the extension of $P_{2U}$ sequence, 25 pMol of each primer and a thoroughly premixed enzyme solution were effective in obtaining the extended sequence.

Amplification was conducted using the MJ PTC200 (MJ Research, Watertown, Mass.) and the following parameters:

| Step | Condition |
| --- | --- |
| Step 1 | 94° C. for 60 sec (initial denaturation) |
| Step 2 | 94° C. for 15 sec |
| Step 3 | 65° C. for 1 min |
| Step 4 | 68° C. for 7 min |
| Step 5 | Repeat step 2–4 for 15 additional times |
| Step 6 | 94° C. for 15 sec |
| Step 7 | 65° C. for 1 min |
| Step 8 | 68° C. for 7 min + 15 sec/cycle |
| Step 9 | Repeat step 6–8 for 11 additional times |
| Step 10 | 72° C. for 8 min |
| Step 11 | 4° C. (and holding) |

At the end of 28 cycles, 50 µl of the reaction mix was removed; and the remaining reaction mix was run for an additional 10 cycles as outlined below:

| Step | Condition |
| --- | --- |
| Step 1 | 94° C. for 15 sec |
| Step 2 | 65° C. for 1 min |
| Step 3 | 68° C. for (10 min + 15 sec)/cycle |
| Step 4 | Repeat step 1–3 for 9 additional times |
| Step 5 | 72° C. for 10 min |

A 5–10 µl aliquot of the reaction mixture was analyzed on a mini-gel to determine successful reactions. Although all extended cDNA species potentally contained the full length gene, some of the largest products were selected and separated from template by electrophoresis on a low concentration (about 0.6–0.8%) agarose gel. The bands representing the gene of interest were cut out of the gel and purified using a method like the QIAQuick™ gel extraction kit (QIAGEN Inc, Chatsworth, Calif.). Klenow enzyme was used to convert eventual overhangs into blunt ends to facilitate religation and cloning of the products.

After ethanol precipitation, the products were redissolved in 13 µl of ligation buffer. Then, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium. After incubation for one hour at 37° C., the whole transformation mixture was plated on LB-agar containing 2× carbenicillin.

The following day, 12 colonies were randomly picked from each plate and cultured in 150 µl of liquid LB/carbenicillin medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 15 µl of PCR mix (1.33× concentrated containing 0.75 units of Taq polymerase, a vector primer and one or both of the gene specific primers used for the extension reaction) were added to each well. Amplification was performed using the following conditions:

| Step | Condition |
| --- | --- |
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 times |
| Step 6 | 72° C. for 180 sec |
| Step 7 | 4° C. (and holding) |

Aliquots of these PCR reactions were run on agarose gels together with molecular weight markers. The sizes of the PCR products were compared to the original partial cDNAs, and appropriate clones were selected, ligated into plasmid and sequenced.

The cDNA (SEQ ID NO 1) and amino acid (SEQ ID NO 2) sequences for human PNR are shown in FIG. 1. When the translation of the sequence was searched against protein databases such as SwissProt and PIR, no exact matches were found. FIG. 2 shows the comparison of the human PNR sequence with that of the rat purinergic sequence, RNU09402.

VI Antisense Analysis

Knowledge of the correct, complete cDNA sequence of PNR enables its use as a tool for antisense technology in the investigation of gene function. Oligonucleotides, cDNA or genomic fragments comprising the antisense strand of pnr can be used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest can be effectively turned off. Frequently, the function of the gene can be ascertained by observing behavior at the intracellular, cellular, tissue or organismal level (eg, lethality, loss of differentiated function, changes in morphology, etc).

In addition to using sequences constructed to interrupt transcription of a particular open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of PNR

Expression of pnr may be accomplished by subcloning the cDNAs into appropriate expression vectors and transfecting the vectors into analogous expression hosts. In this particular case, the cloning vector previously used for the generation of the cDNA library also provides for direct expression of pnr sequences in E. coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or the inclusion of an oligonucleotide linker of appropriate length.

The pnr cDNA can be shuttled into other vectors known to be useful for expression of protein in specific hosts. Oligonucleotide primers containing cloning sites as well as a segment of DNA (about 25 bases) sufficient to hybridize to stretches at both ends of the target cDNA can be synthesized chemically by standard methods. These primers can then be used to amplify the desired gene segment by PCR. The resulting gene segment can be digested with appropriate restriction enzymes under standard conditions and isolated by gel electrophoresis. Alternately, similar gene segments can be produced by digestion of the cDNA with appropriate restriction enzymes. Using appropriate primers, segments of coding sequence from more than one gene can be ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, may be used in mammalian host cells. Once homogeneous cultures of recombinant cells are obtained through standard culture methods, large quantities of recombinantly produced PNR can be recovered from the conditioned medium and analyzed using chromatographic methods known in the art.

VIII Isolation of Recombinant PNR

PNR may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego, Calif.) between the purification domain and the pnr sequence may be useful to facilitate expression of PNR.

IX Testing of $P_{2U}$ Receptors

The procedures for testing purinergic receptors were published by Erb et al (1993, Proc Natl Acad Sci 90:10449–53). The function of PNRs can easily be tested in cultured K562 human leukemia cells because these cells lack $P_{2U}$ receptors. K562 cells are transfected with expression vectors containing pnr and loaded with fura-a, fluorescent probe for $Ca^{++}$. Activation of properly assembled and functional $P_{2U}$ receptors with extracellular UTP or ATP mobilizes intracellular $Ca^{++}$ which reacts with fura-a and is measured spectrofluorometrically. In addition these procedures can be used to define the affinity and effective concentration of those extracellular nucleotides which activate such receptors. Likewise, chimeric receptors—combining extracellular receptive sequences of any newly T7G—with the transmembrane and intracellular segments of a known molecule such as pnr are useful in defining potential ligands for the new molecule.

Chimeric or modified $P_{2U}$ receptors containing substitutions in the transmembrane or intracellular regions may be activated using UTP and the resulting biological activity assessed. Once function is established, the amino- or carboxy-terminal residues are useful in testing antagonists or inhibitors of intracellular $Ca^{++}$ release or phosphoinositide metabolism.

X Production of PNR Specific Antibodies

Two approaches are utilized to raise antibodies to PNR, and each approach is useful for generating either polyclonal or monoclonal antibodies. In one approach, denatured protein from reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of an appropriate PNR domain, as deduced from translation of the cDNA, is analyzed to determine regions of high immunogenicity. Oligopeptides comprising appropriate hydrophilic regions, as illustrated in FIG. 3, are synthesized and used in suitable immunization protocols to raise antibodies. Analysis to select appropriate epitopes is described by Ausubel F M et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St Louis, Mo.) by reaction with M-maleimidobenzoyl-N- hydroxysuccinimide ester (MBS; cf. Ausubel F M et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled PNR to identify those fusions producing the monoclonal antibody with the desired specificity. In a typical protocol, wells of plates (FAST; Becton-Dickinson, Palo Alto, Calif.) are coated during incubation with affinity purified, specific rabbit-anti-mouse (or suitable anti-species Ig) antibodies at 10 mg/ml. The coated wells are blocked with 1% BSA, washed and incubated with supernatants from hybridomas. After washing the wells are incubated with labeled PNR at 1 mg/ml. Supernatants with specific antibodies bind more labeled PNR than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

XI Diagnostic Test Using PNR Specific Antibodies

Particular PNR antibodies are useful for investigating signal transduction, and the diagnosis of infectious or hereditary conditions which are characterized by differences in the amount or distribution of PNR or downstream products of an active signalling cascade. Since PNR was found in a human placenta library, it appears to be upregulated in cell types mainly involved in immune protection or defense.

Diagnostic tests for PNR include methods utilizing antibody and a label to detect PNR in human body fluids, membranes, cells, tissues or extracts of such. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound PNR, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on PNR is preferred, but a competitive binding assay may be employed. These assays are described, among other places, in Maddox, D E et al (1983, J Exp Med 158:1211f).

XII Purification of Native PNR Using Specific Antibodies

Native or recombinant PNR can be purified by immunoaffinity chromatography using antibodies specific for PNR. In general, an immunoaffinity column is constructed by covalently coupling the anti-PNR antibody to an activated chromatographic resin. Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia, Piscataway N.J.). The antibody is coupled to the resin, the resin is blocked, and the derivative resin is washed according to the manufacturer's instructions.

Such immunoaffinity columns may be utilized in the purification of PNR by preparing a fraction from cells containing PNR in a soluble form. This preparation may be derived by solubilization of whole cells or of a subcellular fraction obtained via differential centrifugation (with or without addition of detergent) or by other methods well known in the art. Alternatively, soluble PNR containing a signal sequence may be secreted in useful quantity into the medium in which the cells are grown.

A soluble PNR-containing preparation is passed over the immunoaffinity column, and the column is washed under conditions that allow the preferential absorbance of PNR (eg, high ionic strength buffers in the presence of detergent). Then, the column is eluted under conditions that disrupt antibody/PNR binding (eg, a buffer of pH 2–3 or a high concentration of a chaotrope such as urea or thiocyanate ion), and PNR is collected.

XIII Drug Screening

This invention is particularly useful for screening therapeutic compounds by using PNR or binding fragments thereof in any of a variety of drug screening techniques. The polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between PNR and the agent being tested. Alternatively, one can examine the diminution in complex formation between PNR and a receptor caused by the agent being tested.

Thus, the present invention provides methods of screening for drugs or any other agents which can affect signal transduction. These methods, well known in the art, comprise contacting such an agent with PNR polypeptide or a fragment thereof and assaying (i) for the presence of a complex between the agent and the PNR polypeptide or fragment, or (ii) for the presence of a complex between the PNR polypeptide or fragment and the cell. In such competitive binding assays, the PNR polypeptide or fragment is typically labeled. After suitable incubation, free PNR polypeptide or fragment is separated from that present in bound form, and the amount of free or uncomplexed label is a measure of the ability of the particular agent to bind to PNR or to interfere with the PNR and agent complex.

Another technique for drug screening provides high throughput screening for compounds having suitable binding affinity to the PNR polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with PNR polypeptide and washed. Bound PNR polypeptide is then detected by methods well known in the art. Purified PNR can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PNR specifically compete with a test compound for binding to PNR polypeptides or fragments thereof. In this manner, the antibodies can be used to detect the presence of any peptide which shares one or more antigenic determinants with PNR.

XIV Rational Drug Design

The goal of rational drug design is to produce structural analogs of biologically active polypeptides of interest or of small molecules with which they interact, eg, agonists, antagonists, or inhibitors. Any of these examples can be used to fashion drugs which are more active or stable forms of the polypeptide or which enhance or interfere with the function of a polypeptide in vivo (cf. Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design efficient inhibitors. Useful examples of rational drug design may include molecules which have improved activity or stability as shown by Braxton S and Wells J A (1992, Biochemistry 31:7796–7801) or which act as inhibitors, agonists, or antagonists of native peptides as shown by Athauda S B et al (1993 J Biochem 113:742–46), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id can then be used to identify and isolate peptides from banks of chemically or biologically produced peptides. The isolated peptides then act as the pharmacore.

By virtue of the present invention, sufficient amount of polypeptide may be made available to perform such analytical studies as X-ray crystallography. In addition, knowledge of the PNR amino acid sequence provided herein will provide guidance to those employing computer modeling techniques in place of or in addition to x-ray crystallography.

XV Identification of Other Members of the Signal Transduction Complex

The inventive purified PNR is a research tool for identification, characterization and purification of interacting G or other signal transduction pathway proteins. Radioactive labels are incorporated into a selected PNR domain by various methods known in the art and used in vitro to capture interacting molecules. A preferred method involves labeling the primary amino groups in PNR with 1251 Bolton-Hunter reagent (Bolton, A E and Hunter, W M (1973) Biochem J 133: 529). This reagent has been used to label various molecules without concomitant loss of biological activity (Hebert C A et al (1991) J Biol Chem 266: 18989; McColl S et al (1993) J Immunol 150:4550–4555). Membrane-bound molecules are incubated with the labeled PNR molecules, washed to removed unbound molecules, and the PNR complex is quantified. Data obtained using different concentrations of PNR are used to calculate values for the number, affinity, and association of PNR complex.

Labeled PNR is also useful as a reagent for the purification of molecules with which PNR interacts. In one embodiment of affinity purification, PNR is covalently coupled to a chromatography column. Cells and their membranes are extracted, PNR is removed and various PNR-free subcomponents are passed over the column. Molecules bind to the column by virtue of their PNR affinity. The PNR-complex is recovered from the column, dissociated, and subjected to N-terminal protein sequencing. This amino acid sequence is then used to identify the captured molecule or to design degenerate oligonucleotide probes for cloning its gene from an appropriate cDNA library.

In another alternate method, antibodies are raised against PNR, specifically monoclonal antibodies. The monoclonal antibodies are screened to identify those which inhibit the binding of labeled PNR. These monoclonal antibodies are then used in affinity purification or expression cloning of associated molecules.

Other soluble binding molecules are identified in a similar manner. Labeled PNR is incubated with extracts or other appropriate materials derived from mast cells and putative target cells. After incubation, PNR complexes (which are larger than the lone PNR molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XVI Administration of Antibodies, Inhibitors, or Antagonists of PNR

Antibodies, inhibitors, or antagonists of PNR (or other molecules to limit signal transduction, LST), can provide different effects when administered therapeutically. LSTs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of LSTs include solubility of the molecule, half-life and antigenicity/immunogenicity; these and other characteristics may aid in defining an effective carrier. Native human proteins are preferred as LSTs, but organic or synthetic molecules resulting from drug screens may be equally effective in particular situations.

LSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the LST to be administered, and the pharmacokinetic profile of the particular LST. Additional factors which may be taken into account include disease state (e.g. severity) of the patient, age, weight, gender, diet, time and frequency of administration, drug combination, reaction sensitivities, and tolerance/response to therapy. Long acting LST formulations might be administered every 3 to 4 days, every week, or once every two weeks depending on half-life and clearance rate of the particular LST.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for different LSTs. Administration to particular cell types will necessitate different methods of delivery, ie. vascular endothelial cells versus glial cells.

It is contemplated that abnormal signal transduction and the conditions or diseases which trigger such activity may precipitate damage that is treatable with LSTs. These conditions or diseases may be specifically diagnosed by the tests discussed above, and such testing should be performed in suspected cases of systemic and local infections, traumatic and other tissue damage, hereditary or environmental diseases associated with hypertension, carcinomas, cystic fibrosis, and other physiologic or pathologic problems.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended. to be within the scope of the following claims.

What is claimed is:

1. A purified purinergic P2U receptor (PNR) polypeptide comprising the amino acid sequence shown in SEQ ID NO:2.

2. A purified purinergic P2U receptor (PNR) polypeptide consisting of the amino acid sequence shown in SEQ ID NO:2.

3. A purified, immunologically active polypeptide comprising at least 17 contiguous amino acids of the sequence shown in SEQ ID NO:2.

* * * * *